United States Patent [19]

Kabbe et al.

[11] 4,405,644

[45] Sep. 20, 1983

[54] MEDICAMENTS FOR THE TREATMENT OF DISORDERS OF LIPOMETABOLISM AND THEIR USE

[75] Inventors: Hans-Joachim Kabbe, Leverkusen; Erich Klauke, Odenthal; Hans P. Krause, Wuppertal; Mithat Mardin, Wuppertal; Rüdiger Sitt, Wuppertal, all of Fed. Rep. of Germany

[73] Assignee: Bayer Aktiengesellschaft, Leverkusen, Fed. Rep. of Germany

[21] Appl. No.: 331,712

[22] Filed: Dec. 17, 1981

Related U.S. Application Data

[63] Continuation of Ser. No. 164,387, Jun. 30, 1980, abandoned.

[30] Foreign Application Priority Data

Jul. 14, 1979 [DE] Fed. Rep. of Germany ....... 2928485

[51] Int. Cl.³ .................... A61K 31/275; A61K 31/17
[52] U.S. Cl. .................................... 424/322; 424/304; 260/465 D; 564/48; 564/49; 564/52; 564/53; 564/54; 564/55
[58] Field of Search ............................... 424/322, 304; 260/465 D; 564/48, 49, 52, 53, 54, 55

[56] References Cited

U.S. PATENT DOCUMENTS

| 2,688,039 | 8/1954 | Huebner et al. | 260/454 |
| 2,745,874 | 5/1956 | Schetty et al. | 564/54 |
| 2,983,646 | 5/1961 | Ruboff | 564/53 |
| 3,200,035 | 8/1965 | Martin | 564/54 |
| 3,230,141 | 1/1966 | Frick et al. | 564/54 |
| 3,335,142 | 8/1967 | Hardy et al. | 71/94 |
| 3,340,145 | 9/1967 | Martin | 564/54 |
| 3,689,550 | 9/1972 | Schellenbaum et al. | 424/322 |
| 3,856,952 | 12/1974 | Huber | 424/233 |
| 3,860,645 | 1/1975 | Nikawitz | 424/322 |
| 3,903,130 | 9/1975 | Teach | 260/465 D |
| 4,011,340 | 3/1977 | Nadelson | 424/322 |

FOREIGN PATENT DOCUMENTS 1219698  1/1971  United Kingdom ................. 564/53

OTHER PUBLICATIONS

Beaver et al. J.A.C.S. 1957, p. 1236.
Emerson et al., CA. 94:71498D.

*Primary Examiner*—Jane T. Fan
*Attorney, Agent, or Firm*—Sprung, Horn, Kramer & Woods

[57] ABSTRACT

The invention relates primarily to pharmaceutical compositions and medicaments containing a compound of Formula (I), infra as the active ingredient. Also included in the invention are methods for combatting lipometabolic illnesses by administration of an active compound of the invention alone, in combination with a diluent or in the form of a medicament.

9 Claims, No Drawings

MEDICAMENTS FOR THE TREATMENT OF DISORDERS OF LIPOMETABOLISM AND THEIR USE

This is a continuation of application Ser. No. 164,387, filed June 30, 1980 now abandoned.

The present invention relates to the use as agents for influencing the lipid metabolism of certain urea derivatives some of which are known.

Some of the urea derivatives which can be used according to the invention are already known (see DT-OS (German Published Specification) 1,443,560; U.S. Pat. No. 3,335,142; U.S. Pat. No. 3,856,952 and U.S. Pat. No. 3,903,130). Some biological actions have also been described for these known urea derivatives. For example, they can be used as herbicides, bactericides, fungicides and feed additives. Their pharmaceutical action on lipometabolism, in particular their inhibiting action on lipid absorption, has not hitherto been disclosed.

According to the present invention there are provided pharmaceutical compositions containing as an active ingredient a compound which is an urea derivative of the formula

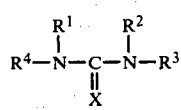

(I)

in which
R$^1$ and R$^2$ are identical or different and in each case represent a hydrogen atom, a straight-chain, branched or cyclic alkyl, aryl or aralkyl radical, the alkyl and aryl radicals mentioned being optionally substituted by halogen or alkoxy,
R$^3$ and R$^4$ are identical or different and in each case represent an aryl or hetero-aryl radical, these radicals optionally being substituted by 1, 2, 3 or 4 identical or different substituents selected from nitro, cyano, halogen, azido, hydroxyl, amino, carboxyl, aminocarbonyl, aminosulphonyl (the amino groups in each case being optionally monosubstituted or disubstituted by alkyl or aryl), alkoxycarbonyl, acyloxy (preferably alkanoyloxy), acylamino (preferably alkanoylamino), SO-alkyl, SO$_2$-alkyl, acyl, phenyl, phenoxy, phenylmercapto, alkyl, alkoxy and alkylmercapto, the alkyl, alkoxy and alkylmercapto radicals mentioned being in turn optionally substituted by 1 or more fluorine atoms; the phenyl, phenylmercapto and phenoxy substituents mentioned being in turn optionally substituted by halogen, alkyl, alkoxy or alkylmercapto (these alkyl, alkoxy and alkylmercapto radicals being optionally monosubstituted or polysubstituted by fluorine); or two adjacent substituents on the aryl radical, together with the two carbon atoms on which they are positioned, representing a dioxane or dioxole ring which is optionally substituted by fluorine, and
X represents an oxygen or sulphur atom or a cyanamide group, in admixture with an inert pharmaceutical carrier, such as a solid or liquefied gaseous diluent or in admixture with a liquid diluent other than a solvent of a molecular weight less than 200 except in the presence of a surface-active agent.

As used herein, and unless otherwise specified the term "alkyl" preferably has 1 to 8 carbon atoms in a straight or branched chain; the term "alkoxy" and "alkylmercapto" also preferably have 1 to 8 carbon atoms; the term "cyclic alkyl" preferably refers to cyclic alkyl having 4 to 7, preferably 5 to 6 carbon atoms; the term "aryl" preferably refers to mono- or bi-cyclic carbocyclic aryl, such as particularly phenyl but also biphenyl or naphthyl; the term "aralkyl" preferably refers to substituents in which the aryl portion is defined as immediately above for "aryl" and the alkyl portion contains 1 to 4, preferably 1 to 2 carbon atoms; the term "hetero-aryl" preferably refers to pyridyl.

The pharmaceutical compositions of the present invention are useful in the treatment of lipometabolic illnesses. The present invention also relates to medicaments which influence lipometabolism, and to some new compounds from this group of substances which are active ingredients in the pharmaceutical compositions of the present invention.

Surprisingly, the urea derivatives of the general formula (I) exhibit a powerful inhibiting action on lipid absorption. A knowledge of the prior art could not lead one to expect that compounds of this group of substances can be used as active compounds which inhibit lipid absorption. From the use as feed additives, which is already known in animal husbandry, and the bactericidal action, it could be expected that after administration, the body absorbs foodstuff to an increased extent, which leads to the increase in weight desired in animal husbandry. The discovery of inhibiting action on lipid absorption and the resulting possibility of using the urea derivatives as additives to foodstuffs and of inhibiting absorption of lipids from foodstuffs by administration of appropriate medicament formulations represent the removal of a prejudice resulting from the state of the art.

The use of urea derivatives in the treatment of hyperlipaemia enables those patients who show intolerance or habituation towards the lipid absorption inhibitors already known also to be treated. The use of the urea derivatives for the first time as active compounds in the treatment of hyperlipaemia thus represents an enrichment of pharmacy.

The urea derivatives of the general formula (I) are prepared in a manner which is in itself known, by a process in which
(a) an amine of the formula

(II)

in which
R$^1$ and R$^4$ have the meaning indicated above, is reacted with a compound of the formula

(III)

in which
R$^3$ and X have the meaning indicated above, in an inert organic solvent at temperatures between 20° C. and 120° C. [reaction variant (a) gives symmetric and unsymmetric urea derivatives in which R$^2$ always denotes hydrogen], or
(b) an amine of the formula $$\begin{array}{c} R^1 \\ | \\ R^4-NH \end{array} \quad (II)$$

in which
R$^1$ and R$^4$ have the meaning indicated above,
is reacted with chloroformic acid phenyl ester of the formula $$ClCOOC_6H_5 \quad (IV)$$

at temperatures between 0° and 25° C. and the carbamic acid phenyl ester thereby formed, of the formula $$\begin{array}{c} R^1 \\ | \\ R^4-N-COOC_6H_5 \end{array} \quad (V)$$

is reacted directly, or after isolation with an amine of the formula $$\begin{array}{c} R^2 \\ | \\ R^3-NH \end{array} \quad (VI)$$

in which
R$^2$ and R$^3$ have the meaning indicated above,
in an inert organic solvent at temperatures between 20° C. and 200° C. [reaction variant (b) gives urea derivatives in which X denotes oxygen], or
(c) a thioester of the formula $$\begin{array}{c} R^1 \\ | \\ R^4-N-C-S\ Alkyl \\ \phantom{R^4-N-}\| \\ \phantom{R^4-N-}X \end{array} \quad (VII)$$

in which
R$^1$ and R$^4$ have the meaning indicated above and
X represents a sulphur atom or a cyanamide group,
is reacted with an amine of the formula $$\begin{array}{c} R^2 \\ | \\ R^3-NH \end{array} \quad (VI)$$

in which
R$^2$ and R$^3$ have the meaning indicated above,
optionally in the presence of an inert organic solvent at temperatures between 20° and 180° C., until the alkylmercaptan evolution has ended, or
(d) each mol of a compound of the formula $$X = C \diagup^{Y}_{\diagdown Y'} \quad (VIII)$$

in which
X has the meaning indicated above and
Y and Y' are identical or different and represent a radical which can be replaced nucleophilically under the reaction conditions, such as chlorine, alkylmercapto or phenoxy,
is reacted with 2 moles of an amine of the formula $$\begin{array}{c} R^1 \\ | \\ R^4-NH \end{array} \quad (II)$$

in which
R$^1$ and R$^4$ have the meaning indicated above, optionally in the presence of an inert organic solvent [reaction variant (d) always gives symmetric urea derivatives in which, in each case, R$^1$ and R$^2$, and R$^3$ and R$^4$ are identical].

In the above process variants (a), (b), (c) and (d), the amines of the formula (II) and of the formula (VI) can in each case be employed as alternatives to each other, if the meaning of R$^1$ and R$^4$ or of R$^2$ and R$^3$ in the particular reactant lead to the desired product.

Particularly preferred urea derivatives of the formula (I) for use according to the present invention are those in which R$^1$ and R$^2$ are identical or different and in each case represent a hydrogen atom, a straight-chain or branched alkyl radical (with 1 to 4 carbon atoms), a phenyl radical or a benzyl radical, the alkyl and phenyl radicals (including the phenyl portion of the benzyl radicals) mentioned being optionally substituted by fluorine or chlorine, R$^3$ and R$^4$ are identical or different and in each case represent a phenyl or naphthyl radical, these radicals, and preferably the phenyl radical, optionally being substituted by 1, 2, 3 or 4 identical or different substituents selected from nitro, cyano, halogen (in particular fluorine or chlorine), azido, hydroxyl, amino, carboxyl, aminocarbonyl, aminosulphonyl (the amino groups in each case optionally being substituted by alkyl with 1 to 8 carbon atoms or phenyl), phenyl, phenoxy, alkoxycarbonyl with 1 to 8 carbon atoms, acyloxy (particularly alkanoyloxy) with 1 to 8 carbon atoms, acylamido (particularly alkanoylamido) with 1 to 8 carbon atoms, acyl particularly alkanoyl with 1 to 8 carbon atoms and SO$_2$-alkyl with 1 to 8 carbon atoms, and from alkyl, alkoxy or alkylmercapto with in each case 1 to 8 carbon atoms (these alkyl, alkoxy and alkylmercapto radicals being in turn optionally mono-substituted or polysubstituted by fluorine), and X represents an oxygen or sulphur atom or the cyanamide group.

The abovementioned alkyl, alkoxy, alkylmercapto and acyl (preferably alkanoyl) radicals preferably contains 1 to 4 carbon atoms.

Particularly preferred compounds of the formula (I) are those for use according to the present invention in which R$^1$ and R$^2$ in each case represent a hydrogen atom and R$^3$ and R$^4$ are identical or different and in each case represent a phenyl radical which is mono-, di-, tri- or tetra-substituted by halogen (in particular fluorine or chlorine), trifluoromethyl, trifluoromethoxy, trifluoromethylmercapto, cyano, carboxyl, alkyl, alkoxy, acyl (particularly alkanoyl) alkoxycarbonyl or dialkylaminosulphonyl (with in each case 1 to 4 carbon atoms in the alkyl, alkoxy and acyl (e.g. alkanoyl) radicals), and X has the meaning indicated above.

Especially preferred urea derivatives of the formula (I) for use according to the present invention are those in which R$^1$ and R$^2$ represent hydrogen atom, X represents an oxygen atom and R$^3$ and R$^4$ in each case represent a phenyl radical which is substituted by 1, 2, or 3 identical or different substituents selected from chlorine, fluorine, cyano, trifluoromethyl, trifluoromethoxy, trifluoromethylmercapto, dialkylaminosulphonyl, alkoxycarbonyl and alkyl (with in each case 1 to 4 carbon atoms in the alkyl and alkoxy radicals).

The novel compounds from the class of substances defined by the formula (I) are likewise prepared according to the above-mentioned process variants (a) to (c), and the isocyanate derivatives, amines and carbamic acid phenyl esters of the formula (III), (IV), (VI) and (VII) used as starting substances are known or they can be prepared by known methods (see R. Wagner et al, Synthetic Organic Chemistry, Wiley, New York, (1953), pages 640, 645, 653).

The urea derivatives according to the formula (I) exhibit an advantageous inhibition of lipid absorption in warm-blooded animals. When fat-containing food is eaten, they lead to a lower alimentary hyperlipaemia and simultaneously inhibit cholesterol absorption, so that they can be used, in particular, for the treatment of disorders in lipometabolism, such as, for example, hyperlipoproteinaemia, arterisoclerosis and adiposity.

As stated above, the invention also relates to the use in medicine of the compounds of the invention.

The invention further provides pharmaceutical compositions containing as active ingredient a compound of the invention in the form of sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and sailicic acid; (b) binding agents, e.g. carboxymethyl cellulose and other cellulose derivatives, alginates, gelatine and polyvinyl pyrrolidone; (c) moisturising agents, e.g. glycerol; (d) disintegrating agents e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol mono-stearate; (h) adsorptive carriers, e.g. kaolin and bentonite; (i) lubricants, e.g. talc, calcium and megnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary inert, pharmaceutical carriers, such as diluents (with of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents; e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95%, of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention as hypolipidemic agents is 250 mg to 5 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), or rectally, preferably orally or parenterally, especially orally. Preferred pharmaceutical compositions and medicaments are therefore those adapted for administration such as oral administration. Administration in the method of the invention is preferably oral administration.

In general it has provided advantageous to administer, for hydrolipidemic effect, amounts of from 1.0 to 500, preferably 5 to 100, mg/kg of body weight per day, divided into 1 to 6 administrations, before and/or during and/or after meals, to achieve effective results. A single administration preferably contains the active compound or compounds in amounts of 1 to 100 mg/kg of body weight. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following formulation Examples illustrate the preparation of medicament formulations to be used according to the invention.

EXAMPLES FOR THE PREPARATION OF TABLETS 1. 100 mg of the compound of Example 1 are mixed with 69 mg of lactose and 30 mg of maize starch and the mixture is then kneaded with a paste of 15 mg of maize starch and forced through a sieve of 3–5 mm mesh width. The mixture is then dried at 60°–80° C. in a drier.

The resulting granules are passed through a sieve of 0.8 mm mesh width, a further 15 mg of maize starch, 10 mg of talc and 1 mg of magnesium stearate are admixed and the mixture is pressed to round tablets with a diameter of 9 mm and a total weight of 240 mg with the aid of a customary tablet press.

2. 200 mg of the compound of Example 29 are mixed with 97 mg of secondary calcium phosphate and the mixture is kneaded with aqueous gelatine solution containing 2 mg of gelatine. The mixture is then forced through a sieve of 3–5 mm mesh width and dried at 60°–80° C. The dry granules are sieved (0.8 mm), 20 mg of wheat starch and 1 mg of magnesium stearate are admixed and the mixture is pressed to tablets in a known manner. Round tablets with a diameter of 8 mm and a total weight of 320 mg are obtained.

The advantageous action of compounds used according to the present invention in inhibiting lipid absorption is illustrated in the following experiment, using rats.

Example A

To produce alimentary hyperlipaemia, 2.5 ml/kg of olive oil are administered perorally to a group of rats (control group). At the same time as the administration of olive oil, the active substances was administered as a suspension in gum tragacanth to a corresponding group of other rats, using a stomach tube. Gum tragacanth by itself if administered to a further control group of rats.

2 Hours after the administration of olive oil, the concentrations of the serum triglycerides in all three groups of rats is determined (method: J. Ziegenhorst, Klin. Chem. 21, (1975) 1,627). Two hours after administration of the fat, a significant increase in the serum triglycerides is found in the rats treated only with olive oil (group 1), compared with rats to which no fat is administered (group 3). This increase, which is put equal to 100%, is compared with the lower increases of serum triglycerides in the animals treated with active substance and olive oil (group 2). It is thus, found that small dosages of the urea derivatives according to formula (I) already cause a significant decrease in serum triglycerides. In addition to the powerful inhibiting action on lipid absorption, the compounds also exhibited an exceptionally good tolerance.

The following Examples illustrate the preparation of the active compounds which can be used according to the present invention. In these Examples the following abbreviations have the following meaning: THF=tetrahydrofurane, DMSO=dimethylsulphoxide and Tol=toluene.

Example 1 (variant a)

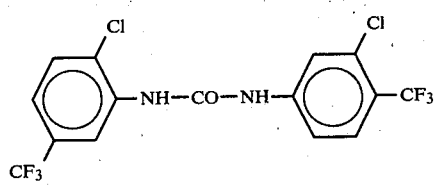

0.05 mol of 2-chloro-5-trifluoromethylaniline is dissolved in 30 ml of tetrahydrofurane and the solution is stirred with a solution of 0.05 mol of 3-chloro-4-trifluoromethylphenyl isocyanate in 30 ml of tetrahydrofurane. The reaction mixture is warmed to 50° C., whereupon the N-2-chloro-5-trifluoromethylphenyl-N'-3-chloro-4-trifluoromethylphenyl-urea precipitates. Melting point 210°–212° C.; yield: 82% of theory.

Example 2 (variant b)

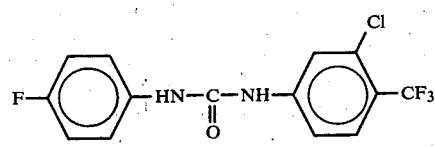

0.5 mol of chloroformic acid phenyl ester is added to a solution of 0.5 mol of p-fluoroaniline in 300 ml of dichlorobenzene and 70 ml (0.5 mol) of triethylamine, whilst cooling (0°–10° C.). The reaction mixture is then left to stand at room temperature for 24 hours. The triethylamine hydrochloride which has formed is filtered off and 0.5 mol of 3-chloro-4-trifluoromethylaniline is added to the filtrate. The reaction solution is heated to 180° C. for 6 hours, the solvent is stripped off in vacuo and the residue is boiled up in 250 ml of ether and filtered off again. N-4-Fluorophenyl-N'-3-chloro-4-trifluoromethylphenylurea of melting point 212° to 214° C. is obtained.

Yield: 67% of theory.

Example 3 (variant c)

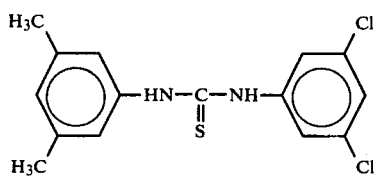

30 ml of triethylamine are added to a solution of 0.2 mol of 3,5-dichloroaniline in 150 ml of tetrahydrofurane. 0.25 mol of carbon disulphide are added dropwise, the mixture is heated to 50°–60° C. for 5 hours and cooled to 20° C. and 0.25 mol of methyl iodide is then added. After stirring the mixture at 20°–25° C. for 2 hours, 200 ml of xylene are added, the organic phase is extracted by shaking with water and then concentrated and 0.2 mol of 3,5-dimethylaniline is added to the residue. The reaction mixture is then heated to 80°–140° C. until the evolution of methylmercaptan subsided. N-3,5-Dichlorophenyl-N'-3,5-dimethylphenyl-thiourea is obtained and is filtered off after cooling.

Melting point: 265°–267° C.; yield: 49% of theory.

Example 4 (variant d)

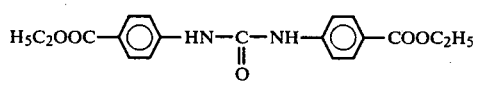

A mixture of 0.2 mol of p-aminobenzoic acid ethyl ester, 150 ml of 1,3-dichlorobenzene and 0.1 mol of diphenyl carbonate is heated to 180° C. for 6 hours. The reaction mixture is cooled and, after 24 hours, filtered. Bis-4-ethoxycarbonylphenyl-urea is obtained.

Melting point: 223°–225° C.; yield: 62% of theory.

Example 5 (variant a)

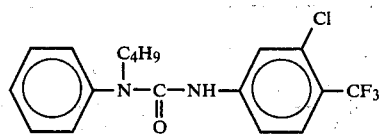

0.05 mol of N-butylaniline in 200 ml of methylene chloride is reacted with 0.05 mol of 4-trifluoromethyl-3-chlorophenyl isocyanate at room temperature. After 12 hours, the precipitate which has separated out is isolated and recrystallized from methanol. N-4-Trifluoromethyl-3-chlorophenyl-N'-butyl-N'-phenyl urea is obtained.

Melting point: 95° C.; yield: 75% of theory.

Example 6 (variant a)

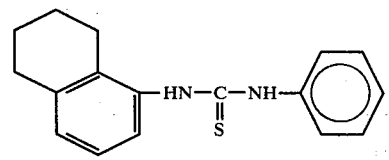

0.1 mol of 5-aminotetralin is dissolved in 30 ml of toluene, and 0.1 mol of phenyl isothiocyanate is added, whereupon the temperature rises to 35° C. and a precipitate forms. The mixture is left to stand for 24 hours and the N-5-tetralyl-N'-phenyl-thiourea is filtered off.

Melting point: 145°–147° C.; yield: 83% of theory.

Unless expressly indicated otherwise, the following tabular examples are prepared according to variant (a), analogously to Example 1:

TABLE 1

$$R^4-NH-\underset{\underset{O}{\parallel}}{C}-NH-R^3 \quad (I\ a)$$

| Example No. | $R^4$ | $R^3$ | Melting point (°C.) | Solvent | Yield (% of theory) |
|---|---|---|---|---|---|
| (7) | 3,5-bis(CF$_3$)-phenyl | 2-Cl, 4-CF$_3$-phenyl | 202–203 | Tol | 72 |
| (8) | 4-Cl, 2-O$_2$N-phenyl | 2-Cl, 4-CF$_3$-phenyl | 125–128 | THF | 91 |
| (9) | 2-NO$_2$, 4-H$_3$C-phenyl | 2-Cl, 4-CF$_3$-phenyl | 243–244 | THF | 64 |

TABLE 1-continued $$R^4-NH-\overset{\underset{\parallel}{O}}{C}-NH-R^3 \quad (1 a)$$

| Example No. | $R^4$ | $R^3$ | Melting point (°C.) | Solvent | Yield (% of theory) |
|---|---|---|---|---|---|
| (10) | 3-Cl, 4-CF$_3$-phenyl | 2-Cl, 4-CF$_3$-phenyl | 263–264 | Tol | 92 |
| (11) | 2-CF$_3$, 4-Cl-phenyl | 2-Cl, 4-CF$_3$-phenyl | 208–210 | Tol | 58 |
| (12) | 2,4-(NO$_2$)$_2$-phenyl | 2-Cl, 4-CF$_3$-phenyl | 164 | DMSO | 51 |
| (13) | 4-O$_2$N-phenyl | 2-Cl, 4-CF$_3$-phenyl | 221 | THF | 87 |
| (14) | 2-Cl, 3-OH, 5-NO$_2$-phenyl | 2-Cl, 4-CF$_3$-phenyl | 135–136 | THF | 70 |
| (15) | 4-CF$_3$-phenyl | 4-OCF$_3$-phenyl | 208–210 | Tol | 79 |
| (16) | 4-Cl, 2-CN-phenyl | 2-Cl, 4-CF$_3$-phenyl | 236–238 | THF | 74 |
| (17) | 4-F$_3$CS-phenyl | 3-CF$_3$, 4-(OCF$_2$O)-phenyl | 205–207 | Tol | 91 |
| (18) | 4-F$_3$CO-phenyl | 3-CF$_3$, 4-(OCF$_2$O)-phenyl | 173–175 | Tol | 93 |
| (19) | 4-F$_3$C-phenyl | 3-CF$_3$, 4-(OCF$_2$O)-phenyl | 200–202 | Tol | 95 |

TABLE 1-continued $$R^4-NH-\overset{\overset{O}{\|}}{C}-NH-R^3 \quad (\text{I a})$$

| Example No. | R⁴ | R³ | Melting point (°C.) | Solvent | Yield (% of theory) |
|---|---|---|---|---|---|
| (20) | 2-Cl, 4-(CF₃)-phenyl | 3-(OCF₂CF₂O fused), phenyl (with F,F on CF) | 249–251 | Tol | 90 |
| (21) | 4-F₃CO-phenyl | 4-OCF₃-phenyl | 215–217 | Tol | 78 |
| (22) | 4-F₃CO-phenyl | 3-Cl, 4-CF₃-phenyl | 189–191 | Tol | 87 |
| (23) | 4-CF₃O-phenyl | 4-SCF₃-phenyl | 239–241 | Tol | 96 |
| (24) | 4-CF₃S-phenyl | 4-SCF₃-phenyl | 267–269 | Tol | 72 |
| (25) | 4-CF₃S-phenyl | 4-CF₃-phenyl | 149–151 | Tol | 68 |
| (26) | 4-CF₃S-phenyl | 3-Cl, 4-CF₃-phenyl | 129–131 | Tol | 96 |
| (27) | 4-CF₃-phenyl | 3-Cl, 4-CF₃-phenyl | 245–247 | Tol | 98 |
| (28) | 4-CF₃-phenyl | 4-CF₃-phenyl | 137–139 | Tol | 89 |
| (29) | 3-CN-phenyl | 3-Cl, 4-CF₃-phenyl | 230–234 | THF | 89 |
| (30) | 3,4-di-CN-phenyl | 3-Cl, 4-CF₃-phenyl | 167–169 | THF | 81 |
| (31) | 2,6-di-Cl-phenyl | 3-Cl, 4-CF₃-phenyl | 243–245 | THF | 64 |
| (32) | 2,6-di-CH₃-phenyl | 3-Cl, 4-CF₃-phenyl | 235–237 | Tol | 75 |
| (33) | 4-CH₃SO₂-phenyl | 3-Cl, 4-CF₃-phenyl | 224–226 | DMSO | 61 |

TABLE 1-continued $$R^4-NH-\overset{\overset{O}{\|}}{C}-NH-R^3 \quad (I\ a)$$

| Example No. | R⁴ | R³ | Melting point (°C.) | Solvent | Yield (% of theory) |
|---|---|---|---|---|---|
| (34) | CH₃CO–C₆H₄– | 3-Cl-4-CF₃-C₆H₃– | 222–225 | THF | 84 |
| (35) | Cl–C₆H₄–O–C₆H₄– | 3-Cl-4-CF₃-C₆H₃– | 215–217 | Tol | 60 |
| (36) | 2,4-F₂-C₆H₃– | 3-Cl-4-CF₃-C₆H₃– | 212–214 | Tol | 86 |
| (37) | 4-F-C₆H₄– | 3-Cl-4-CF₃-C₆H₃– | 212–214 | Tol | 76 |
| (38) | CF₃SO₂–C₆H₄– | 3-Cl-4-CF₃-C₆H₃– | 245–248 | DMSO | 71 |
| (39) | 3-CF₃-4-CF₃S-C₆H₃– | 3-Cl-4-CF₃-C₆H₃– | 197–199 | THF | 82 |
| (40) | 3-CF₃-C₆H₄– | 3-Cl-4-CF₃-C₆H₃– | 184–186 | Tol | 69 |
| (41) | 2,5-Cl₂-4-CN-C₆H₂– | 3-Cl-4-CF₃-C₆H₃– | 255–257 | THF | 70 |
| (42) | 3,4-(CN)₂-C₆H₃– | 3-Cl-4-CF₃-C₆H₃– | 273–275 | THF | 81 |
| (43) | 3,4-Cl₂-C₆H₃– | 3-CF₃-4-Cl-C₆H₃– | 238–240 | Tol | 96 |
| (44) | 2-CO₂C₂H₅-C₆H₄– | 3-Cl-4-CF₃-C₆H₃– | 188–190 | Tol | 88 |
| (45) | 2,6-(CH₃)₂-3,5-(CN)₂-C₆H– | 3-Cl-4-CF₃-C₆H₃– | 190–200 | THF | 48 |
| (46) | 3-CF₃-6-OCH₃-C₆H₃– | 3-Cl-4-CF₃-C₆H₃– | 215–217 | THF | 62 |

TABLE 1-continued
$$R^4-NH-\underset{\underset{O}{\|}}{C}-NH-R^3 \quad (I\ a)$$
| Example No. | R⁴ | R³ | Melting point (°C.) | Solvent | Yield (% of theory) |
|---|---|---|---|---|---|
| (47) |  |  | 218–220 | THF | 93 |
| (48) |  |  | 187–189 | THF | 78 |
| (49) | 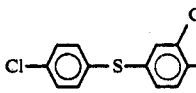 |  | 202–204 | THF | 42 |
| (50) |  |  | 143–46 | Tol | 86 |
| (51) | 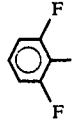 |  | 210–212 | THF | 54 |
| (52) | 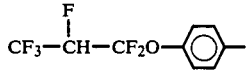 |  | 140–143 | THF | 68 |
| (53) | 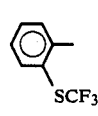 |  | 194–196 | THF | 74 |
| (54) | 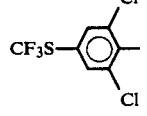 |  | 198–200 | THF | 82 |
| (55) | 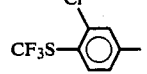 |  | 217–219 | Tol | 88 |
| (56) | 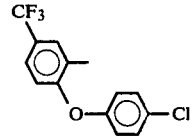 |  | 220–221 | THF | 62 |
| (57) | 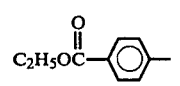 |  | 234–237 | Tol | 84 |
| (58) | 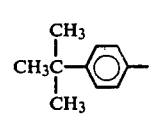 |  | 234 | Tol | 92 |

TABLE 1-continued $$R^4-NH-\overset{\underset{\|}{O}}{C}-NH-R^3 \quad (I\,a)$$

| Example No. | $R^4$ | $R^3$ | Melting point (°C.) | Solvent | Yield (% of theory) |
|---|---|---|---|---|---|
| (59) | ![cyclic sulfonamide with p-tolyl] | 2-Cl, 4-CF$_3$-phenyl | 223 | DMSO | 59 |
| (60) | 3,5-bis(H$_3$COOC)-phenyl | 2-Cl, 4-CF$_3$-phenyl | 200 | THF | 85 |
| (61) | 4-C(CH$_3$)$_3$-phenyl | 4-C(CH$_3$)$_3$-phenyl | 298 | Xylene | 71 |
| (62) | 2,6-di-CH(CH$_3$)$_2$-phenyl | 2,6-di-CH(CH$_3$)$_2$-phenyl | 230 | Dichlorobenzene | 49 |
| (63) | 4-OCH$_3$, 3-CH$_3$, 5-SO$_2$C$_2$H$_5$-phenyl | 2-Cl, 4-CF$_3$-phenyl | 254 | DMSO | 78 |
| (64) | 4-OCH$_3$, 3-SO$_2$C$_6$H$_5$-phenyl | 2-Cl, 4-CF$_3$-phenyl | 258 | DMSO | 80 |
| (65) | 4-OCH$_3$, 3-CH$_2$SO$_2$C$_6$H$_5$-phenyl | 2-Cl, 4-CF$_3$-phenyl | 231 | THF | 72 |
| (66) | 4-C(CH$_3$)$_3$-phenyl | 2,6-di-CH(CH$_3$)$_2$-phenyl | 246 | THF | 89 |
| (67) | 2-NH$_2$, SO$_3$H-phenyl | 2-NH$_2$, SO$_3$H-phenyl | | | |
| (68) | 3,5-bis(H$_3$CO$_2$C)-phenyl | 3,5-bis(CO$_2$CH$_3$)-phenyl | 259 | Dichlorobenzene | 54 |
| (69) | 4-H$_9$C$_4$OOC-phenyl | 2-Cl, 4-CF$_3$-phenyl | 224 | THF | 88 |

TABLE 1-continued $$R^4-NH-C(=O)-NH-R^3 \quad (I\,a)$$

| Example No. | R⁴ | R³ | Melting point (°C.) | Solvent | Yield (% of theory) |
|---|---|---|---|---|---|
| (70) | 4-[(C₃H₇)₂NSO₂]-C₆H₄- | 4-(C(CH₃)₃)-C₆H₄- | 197 | THF | 84 |
| (71) | 4-(C(CH₃)₃)-C₆H₄- | 3,5-(CO₂CH₃)₂-C₆H₃- | 216 | Tol | 66 |
| (72) | 4-[CH₃(CH₂)₁₀CO]-C₆H₄- | 2-Cl-3-CF₃-C₆H₃- | 185 | Tol | 74 |
| (73) | 2,4-bis(ethyl)-6-methyl-1,3,5-triazin-...-yl | 3,4-Cl₂-C₆H₃- | 191–194 | THF | 92 |
| (74) | 3,4-Cl₂-C₆H₃- | 2-CN-4-N(CH₃)₂-C₆H₃- | 193–196 | THF | 80 |
| (75) | 3,5-Cl₂-C₆H₃- | 2-CN-4-(pyrrolidin-1-yl)-C₆H₃- | 226–228 | THF | 76 |
| (76) | 3,4-Cl₂-C₆H₃- | 2-CN-4-(pyrrolidin-1-yl)-C₆H₃- | 222–224 | THF | 79 |
| (77) | 3-Cl-C₆H₄- | 4-(C(CH₃)₃)-C₆H₄- | 178 | Tol | 86 |
| (78) | 3-CF₃-C₆H₄- | 3,4-Cl₂-C₆H₃- | 193 | Tol | 79 |
| (79) | 3-CF₃-C₆H₄- | 4-NO₂-C₆H₄- | | THF | 92 |
| (80) | 3,4-Cl₂-C₆H₃- | 2-NO₂-4-Cl-C₆H₃- | 253 | THF | 95 |
| (81) | 3,4-Cl₂-C₆H₃- | 2-Cl-4-NO₂-C₆H₃- | 276 | THF | 89 |

TABLE 1-continued $$R^4-NH-\underset{\underset{O}{\parallel}}{C}-NH-R^3 \quad (Ia)$$

| Example No. | R⁴ | R³ | Melting point (°C.) | Solvent | Yield (% of theory) |
|---|---|---|---|---|---|
| (82) | 2,5-dichloro-4-methylphenyl | 3-chloro-4-chlorophenyl | 249 | Tol | 95 |
| (83) | 4-methylquinolin-yl | 3-chloro-4-(trifluoromethyl)phenyl | 119–121 | THF | 88 |
| (84) | 5-nitro-4-methylquinolin-yl | 3-chloro-4-(trifluoromethyl)phenyl | 298–300 | DMSO | 76 |
| (85) | 3-(4-methylphenyl)-1-propyltriazenyl | 3-chloro-4-(trifluoromethyl)phenyl | 244–247 | THF | 63 |
| (86) | pyridin-2-yl | 3-chloro-4-(trifluoromethyl)phenyl | 208–310 | THF | 86 |
| (87) | 4-methylpyrimidin-2-yl | 3-chloro-4-(trifluoromethyl)phenyl | 230–231 | THF | 77 |
| (88) | 6-methylquinolin-yl | 3-chloro-4-(trifluoromethyl)phenyl | 258–260 | THF | 81 |
| (89) | pyridin-3-yl | 3-chloro-4-(trifluoromethyl)phenyl | 222–224 | THF | 68 |
| (90) | 4-methylpyridin-yl | 3-chloro-4-(trifluoromethyl)phenyl | 168–171 | THF | 75 |
| (91) | thiazol-2-yl | 3-chloro-4-(trifluoromethyl)phenyl | 179 | DMSO | 65 |
| (92) | benzothiazin-yl | 3-chloro-4-(trifluoromethyl)phenyl | 270 | DMSO | 49 |
| (93) | benzofuran-2-yl-methyl | 3-chloro-4-(trifluoromethyl)phenyl | 270 | THF | 91 |

TABLE 1-continued
R⁴—NH—C(=O)—NH—R³ (I a)
| Example No. | R⁴ | R³ | Melting point (°C.) | Solvent | Yield (% of theory) |
|---|---|---|---|---|---|
| (94) | 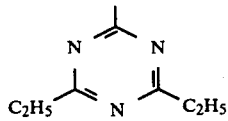 |  | 193–195 | THF | 84 |
| (95) | 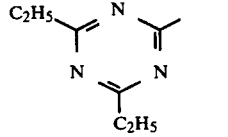 |  | 194–195 | THF | 89 |
| (96) | 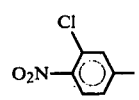 |  | 123–125 | THF | 83 |
| (97) | 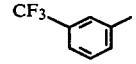 |  | 152–153 | THF | 88 |
| (98) | 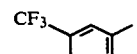 |  | 168–170 | THF | 81 |
| (99) | 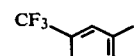 |  | 173–175 | THF | 69 |
| (100) | 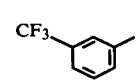 |  | 161–164 | THF | 72 |
| (101) |  |  | 146–147 | THF | 90 |
| (102) |  |  | 225–227 | THF | 93 |
| (103) | 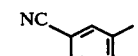 |  | 212–214 | THF | 79 |
| (104) | 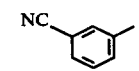 |  | 200–202 | THF | 81 |
| (105) |  |  | 213–215 | THF | 84 |
| (106) |  |  | 116–118 | THF | 90 |
| (107) |  |  | 159–161 | THF | 92 |
| (108) |  |  | 129–131 | THF | 91 |

TABLE 1-continued $$R^4-NH-C(=O)-NH-R^3 \quad (I\ a)$$

| Example No. | R⁴ | R³ | Melting point (°C.) | Solvent | Yield (% of theory) |
|---|---|---|---|---|---|
| (109) | 3-CF₃O-C₆H₄- | 3-SCF₃-C₆H₄- | 124–126 | THF | 72 |
| (110) | 3-CF₃O-C₆H₄- | 2-CF₃-3-Cl-C₆H₃- | 128–131 | THF | 89 |
| (111) | 3-CF₃O-C₆H₄- | 3-CF₃-C₆H₄- | 168–170 | THF | 82 |
| (112) | 3-C₂H₅OOC-C₆H₄- | 3-CF₃-C₆H₄- | 135–137 | THF | 88 |
| (113) | 3-C₂H₅OOC-C₆H₄- | 3-SCF₃-C₆H₄- | 120–121 | THF | 83 |
| (114) | 3-C₂H₅OOC-C₆H₄- | 3,5-Cl₂-C₆H₃- | 213–215 | THF | 72 |
| (115) | 3,5-(CH₃)₂-C₆H₃- | 3,5-Cl₂-C₆H₃- | 265–267 | THF | 89 |
| (116) | 3-NC-C₆H₄- | 3,5-Cl₂-C₆H₃- | 220–222 | THF | 87 |
| (117) | 3-CF₃-C₆H₄- | 3,5-Cl₂-C₆H₃- | 180–182 | THF | 78 |
| (118) | 3,5-Cl₂-C₆H₃- | 3,5-Cl₂-C₆H₃- | 296–298 | THF | 75 |
| (119) | 3-(C₄H₉)₂N-SO₂-C₆H₄- | 3-CN-C₆H₄- | 105–109 | THF | 64 |
| (120) | 3-(C₄H₉)₂N-SO₂-C₆H₄- | 3-COOC₂H₅-C₆H₄- | 108–110 | THF | 91 |
| (121) | 3-(C₄H₉)₂N-SO₂-C₆H₄- | 3,5-(CH₃)₂-C₆H₃- | 106–108 | THF | 79 |
| (122) | 3-(C₄H₉)₂N-SO₂-C₆H₄- | 2,6-Cl₂-C₆H₃- | 165-7 | THF | 94 |
| (123) | 3-(CH₃)₂N-SO₂-C₆H₄- | 3-CN-C₆H₄- | 181-3 | THF | 96 |

TABLE 1-continued

R⁴—NH—C(=O)—NH—R³  (I a)

| Example No. | R⁴ | R³ | Melting point (°C.) | Solvent | Yield (% of theory) |
|---|---|---|---|---|---|
| (124) | " | 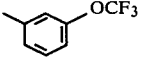 3-OCF₃-phenyl | 173-5 | THF | 84 |
| (125) | " | 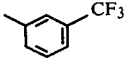 3-CF₃-phenyl | 164-6 | THF | 88 |
| (126) | " | 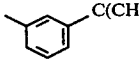 3-C(CH₃)₃-phenyl | 184-6 | THF | 81 |
| (127) | " | 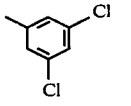 3,5-dichlorophenyl | 198-200 | THF | 83 |
| (128) | 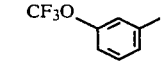 3-CF₃O-phenyl | 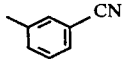 3-CN-phenyl | 167-9 | THF | 78 |
| (129) | 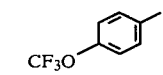 4-CF₃O-phenyl | 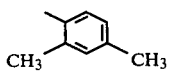 2,4-dimethylphenyl | 211-3 | THF | 81 |
| (130) | 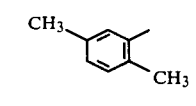 3,4-dimethylphenyl | 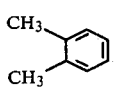 2,3-dimethylphenyl | 221-3 | THF | 84 |
| (131) | 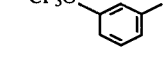 3-CF₃O-phenyl | 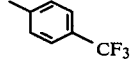 4-CF₃-phenyl | 192-4 | THF | 73 |
| (132) | " | 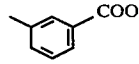 3-COOC₂H₅-phenyl | 139-141 | THF | 90 |
| (133) | 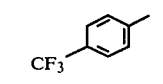 4-CF₃-phenyl | 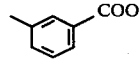 3-COOC₂H₅-phenyl | 173-5 | THF | 81 |
| (134) | " | 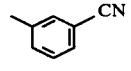 3-CN-phenyl | 216-8 | THF | 95 |
| (135) | 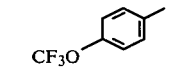 4-CF₃O-phenyl | 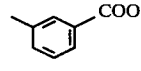 3-COOC₂H₅-phenyl | 163-5 | THF | 79 |
| (136) | " | 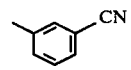 3-CN-phenyl | 178-180 | THF | 99 |
| (137) | " | 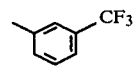 3-CF₃-phenyl | 143-5 | THF | 79 |
| (138) | 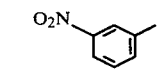 3-O₂N-phenyl | 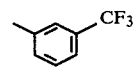 3-CF₃-phenyl | 203-5 | THF | 76 |
| (139) | 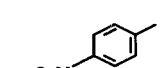 4-O₂N-phenyl | 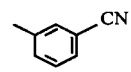 3-CN-phenyl | 238-40 | Tol | 51 |

TABLE 2

$$R^4-\underset{\underset{O}{\|}}{\overset{R^1}{N}}-C-NH-R^3 \quad (Ib)$$

| Example No. | R¹ | R⁴ | R³ | Melting point (°C.) | Solvent | Yield (% of theory) |
|---|---|---|---|---|---|---|
| 140 | phenyl | phenyl | 3-Cl, 4-CF₃ phenyl | 117 | Tol | 81 |
| 141 | (CH₃)₂C(CO₂CH₃)– | phenyl | 3-Cl, 4-CF₃ phenyl | 121 | Tol | 85 |
| 142 | CH₃– | phenyl | 3-Cl, 4-CF₃ phenyl | 95 | Tol | 68 |
| 143 | CH₃– | 4-NO₂ phenyl | 3-Cl, 4-CF₃ phenyl | 187 | Tol | 92 |
| 144 | C₄H₉– | phenyl | 3-Cl, 4-CF₃ phenyl | 97 | Tol | 79 |
| 145 | (CH₃)₂CH–CH₂– | phenyl | 3-Cl, 4-CF₃ phenyl | 101 | Tol | 86 |
| 146 | 4-Cl phenyl | 4-Cl phenyl | 3-Cl, 4-CF₃ phenyl | 225 | THF | 87 |
| 147 | CH₃ | benzothiazol-2-yl | 3-Cl, 4-CF₃ phenyl | 153 | THF | 70 |

TABLE 3

$$R^4-NH-\underset{\underset{S}{\|}}{C}-NH-R^3$$

| Example No. | R⁴ | R³ | Melting point (°C.) | Solvent | Yield (% of theory) |
|---|---|---|---|---|---|
| 148 | phenyl | 2-CN, 6-N(Me)₂ phenyl | 138–139 | THF | 82 |
| 149 | 5,6,7,8-tetrahydronaphth-1-yl | 2-CO₂CH₃, Cl phenyl | 152–154 | THF | 71 |
| 150 | 5,6,7,8-tetrahydronaphth-1-yl | 2-CO₂CH₃, CO₂CH₃ phenyl | 171–175 | THF | 79 |

TABLE 3-continued
$$R^4-NH-\underset{\underset{S}{\|}}{C}-NH-R^3$$
| Example No. | R⁴ | R³ | Melting point (°C.) | Solvent | Yield (% of theory) |
|---|---|---|---|---|---|
| 151 |  | 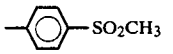 | 167–170 | THF | 84 |
| 152 | 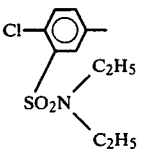 | 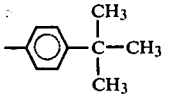 | 115–117 | toluene | 64 |
| 153 | 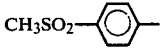 | 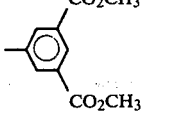 | 251 | toluene | 72 |
| 154 | 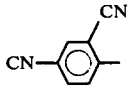 | 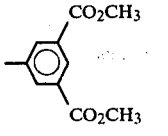 | 190 | toluene | 71 |
| 155 | 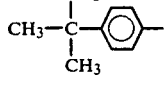 | 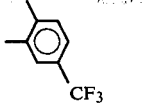 | 182–4 | toluene | 83 |
| 156 | 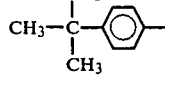 | 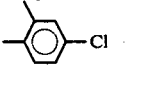 | 167 | toluene | 76 |
| 157 | 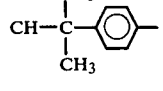 | 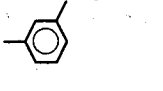 | 194 | toluene | 72 |
| 158 | 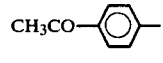 |  | 192 | toluene | 68 |
| 159 | 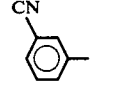 | 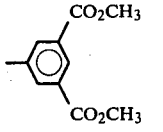 | 209 | toluene | 77 |
| 160 | 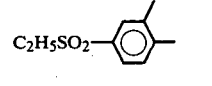 | 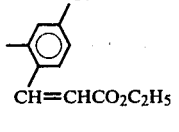 | 211 | toluene | 78 |
| 161 | 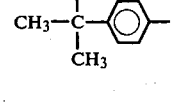 |  | 198 | toluene | 61 |

TABLE 3-continued
$$R^4-NH-\underset{\underset{S}{\parallel}}{C}-NH-R^3$$
| Example No. | R⁴ | R³ | Melting point (°C.) | Solvent | Yield (% of theory) |
|---|---|---|---|---|---|
| 162 | 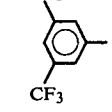 | 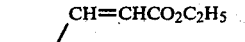 | 205 | toluene | 56 |
| 163 | 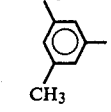 | 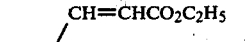 | 178 | toluene | 58 |
| 164 | 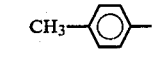 | 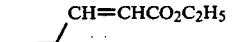 | 168 | toluene | 62 |
| 165 | 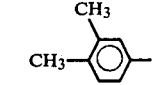 |  | 181 | toluene | 84 |
| 166 |  | 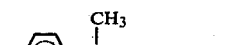 | 201 | toluene | 71 |
| 167 | 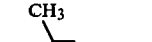 | 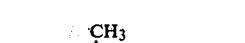 | 231 | toluene | 79 |
| 168 | 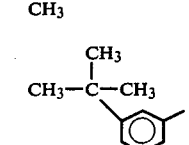 |  | 172 | toluene | 81 |
| 169 | 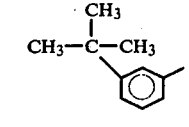 |  | 171 | toluene | 82 |
| 170 | 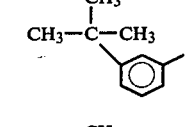 |  | 151 | toluene | 87 |
| 171 | 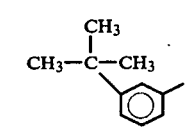 |  | 151 | toluene | 70 |
| 172 | 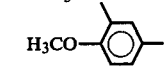 |  | 197 | Chloroform | 68 |
| 173 | 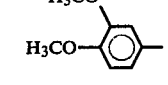 |  | 194 | Chloroform | 81 |

TABLE 3-continued $$R^4-NH-\underset{\underset{S}{\|}}{C}-NH-R^3$$

| Example No. | R⁴ | R³ | Melting point (°C.) | Solvent | Yield (% of theory) |
|---|---|---|---|---|---|
| 174 | H₃CO—, H₃CO—⟨phenyl⟩— | Cl, Cl —⟨phenyl⟩— | 195 | Chloroform | 63 |
| 175 | CH₃, SO₂—N—⟨phenyl⟩—⟨phenyl⟩— | Cl —⟨phenyl⟩— | 166 | Chloroform | 73 |
| 176 | CH₃, SO₂—N—⟨phenyl⟩—⟨phenyl⟩— | Cl —⟨phenyl⟩— | 163 | Chloroform | 68 |
| 177 | CH₃, SO₂—N—⟨phenyl⟩—⟨phenyl⟩— | CF₃ —⟨phenyl⟩— | 202 | Chloroform | 62 |
| 178 | CF₃—⟨phenyl⟩— | OCH₃, —⟨phenyl⟩—OCH₃ | 131 | Chloroform | 81 |
| 179 | ⟨6-methylquinolinyl⟩ | CF₃ —⟨phenyl⟩— | 191 | Chloroform | 76 |
| 180 | ⟨6-methylquinolinyl⟩ | Cl —⟨phenyl⟩— | 290 | Chloroform | 67 |
| 181 | NC—CH₂—CO—⟨phenyl⟩— | CF₃ —⟨phenyl⟩— | 204 | ethyl-acetate | 64 |
| 182 | NC—CH₂—CO—⟨phenyl⟩— | Cl —⟨phenyl⟩— | 229 | ethyl-acetate | 59 |

The present invention also comprises the use of pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A method of combating lipometabolic illnesses in warm-blooded animals which comprises administering to the animals a hypolipidemically effective amount of a urea derivative of the formula

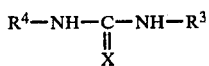

in which

R³ and R⁴ are identical or different and in each case represent a mono-or bi-cyclic carbocyclic aryl radical, optionally substituted by 1 or 2 identical or different substituents selected from cyano, halogen, alkyl, alkoxy and alkylmercapto, the alkyl, alkoxy and alkylmercapto radicals mentioned being in turn substituted by 1 or more fluorine atoms with the proviso that (a) R³ and R⁴ contain a total of 2 or 3 substituents including a total of 1 or 2 halogen substituents (b) R³ and R⁴ are devoid of ortho substituents and (c) R³ and R⁴ are so chosen that p,p'-substituted compounds and m,m'-disubstituted compounds in which the substituents are fluorinated alkyl groups are excluded, and X represents an oxygen or sulphur atom either alone or in admixture with an inert carrier or in the form of a medicament.

2. A method according to claim 1 in which the active compound is administered in an amount of 5 to 100 mg per kg body weight per day.

3. A method according to claims 1 or 2 in which the active compound is administered orally.

4. A method according to claim 1 in which the active ingredient is N-3-trifluoromethylphenyl-N'-3-chloro-4-trifluoromethylphenyl-urea.

5. A method according to claim 1 in which the active ingredient is N-3-trifluoromethoxyphenyl-N'-3-chloro-4-trifluoromethylphenyl urea.

6. A method according to claim 1 in which the active ingredient is N-3-trifluoromethoxyphenyl-N'-3-trifluoromethyl-4-chlorophenyl urea.

7. A method according to claim 1 in which the active ingredient is N-3-trifluoromethoxyphenyl-N'-3-trifluoromethylphenyl urea.

8. A method according to claim 1 in which the active ingredient is N-4-trifluoromethylphenyl-N'-3-cyanophenyl urea.

9. A method according to claim 1 in which the active ingredient is N-4-trifluoromethoxyphenyl-N'-3-cyanophenyl urea.

* * * * *